United States Patent [19]

Moriguchi et al.

[11] Patent Number: 4,879,340

[45] Date of Patent: Nov. 7, 1989

[54] ADSORBENT COMPOSED OF POROUS BEADS OF CHITOSAN AND ADSORPTION METHOD USING SAME

[75] Inventors: Soyao Moriguchi; Hiroshi Suzuki, both of Yokohama; Hiroko Watanabe, Meguro; Motoaki Satoh, Yokosuka; Michio Abe, Sagamihara; Yasuo Iwata, Ota, all of Japan

[73] Assignees: Showa Denko Kabushiki Kaisha; Kawasumi Kagaku Kougiyou Kabushiki Kaisha, both of Tokyo, Japan

[21] Appl. No.: 86,989

[22] Filed: Aug. 19, 1987

[30] Foreign Application Priority Data

Aug. 19, 1986 [JP] Japan .................................. 61-192141
Aug. 19, 1986 [JP] Japan .................................. 61-192142
Aug. 19, 1986 [JP] Japan .................................. 61-192143
Aug. 19, 1986 [JP] Japan .................................. 61-192144
Feb. 18, 1987 [JP] Japan .................................... 62-33472

[51] Int. Cl.$^4$ .................... C08F 283/00; B01J 1/04; C08B 37/08
[52] U.S. Cl. ................................. 525/54.2; 530/351; 530/396; 536/20; 210/656; 210/927
[58] Field of Search ................... 536/20; 525/54.2; 210/656, 927; 127/29; 530/351, 396

[56] References Cited

U.S. PATENT DOCUMENTS 4,409,330 10/1983 Pollard, Jr. ......................... 435/178

Primary Examiner—John Kight
Assistant Examiner—Nathan M. Nutter
Attorney, Agent, or Firm—Sughrue, Mion, Zinn, Macpeak & Seas

[57] ABSTRACT

Disclosed is an adsorbent composed of porous beads of uncrosslinked or crosslinked chitosan, wherein protein A or lectin is covalent-bonded trough a bonding group to the amino group of glucosamine constituting the chitosan in the case of uncrosslinked chitosan or to the amino group of glucosamine constituting the chitosan and an amino group of a crosslinking agent in the case of crosslinked chitosan. The adsorbent composed of the chitosan porous beads to which protein A is bonded through a bonding group is used for absorption removal of interleukin 2 inhibitor. The adsorbent composed of the chitosan porous beads to which lectin is bonded through a combination group is used as an adsorbent for affinity chromatography.

An adsorbent composed of porous beads of uncrosslinked or crosslinked chitosan is used for adsorbing immunoglobulin. An adsorbent composed of uncrosslinked or crosslinked chitosan wherein an ω-carboxylalkanoyl group and an acyl group have been introduced is used as a carrier for chromatography.

22 Claims, 4 Drawing Sheets

← 5mm →

ELUENT A
        ELUENT B

ELUENT A   ELUENT B

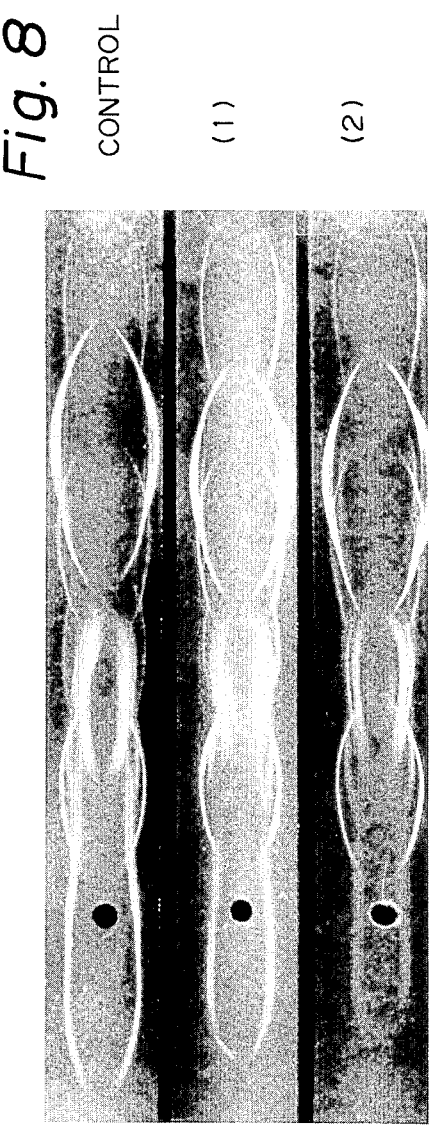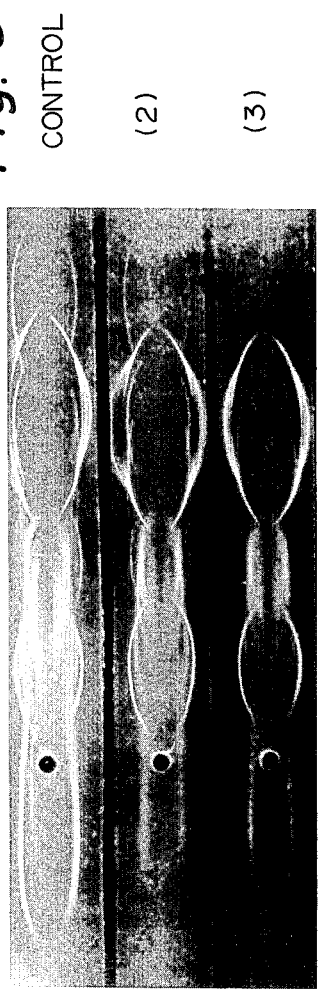

Fig. 10
 CONTROL
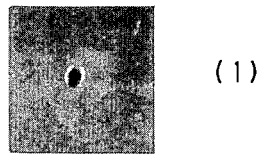 (1)
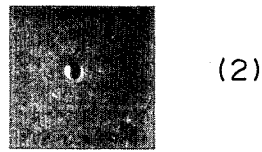 (2)
Fig. 11
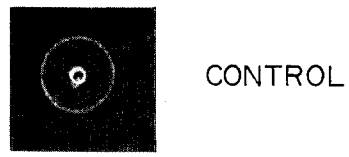 CONTROL
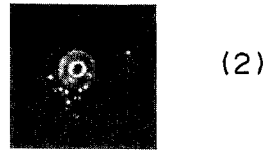 (2)
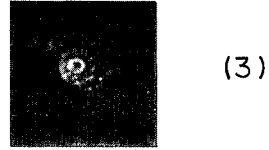 (3)

ADSORBENT COMPOSED OF POROUS BEADS OF CHITOSAN AND ADSORPTION METHOD USING SAME

BACKGROUND OF THE INVENTION (1) Field of the Invention

The present invention relates to an absorbent composed of porous beads of chitosan. More particularly, the present invention relates to an adsorbent composed of porous beads of uncrosslinked or crosslinked chitosan to which protein A or lectin is bonded through a combination group having a carboxyl group.

Furthermore, the present invention relates to a method for removing immunoglobulin by using an adsorbent composed of porous beads of chitosan, and to a method in which adsorption by affinity chromatography or removal of an inhibitor for the activity of interleukin-2 is accomplished by an adsorbent composed of porous beads of uncrosslinked or crosslinked chitosan to which a carboxyl group is bonded, or an adsorbent composed of porous beads of uncrosslinked or crosslinked chitosan to which protein A or lectin is bonded through an amide group.

(2) Description of the Related Art

In affinity chromatography, a chromatographical technique, separation or purification is performed by utilizing the affinity between a pair of substances specifically exerting mutual actions on each other. For example, affinity chromatography is valuable for purifying a biological substance on the basis of a discrimination of a biological characteristic of the biological substance, that is, a specific chemical structure on the molecule.

An adsorbent (i.e., affinity gel) for the affinity chromatography comprises, for example, an active support obtained by bonding a combination group (spacer) to an insoluble carrier (matrix) and a ligand bonded to the spacer. The adsorption operation is performed on a combination of this ligand and a selected substance, which exert mutual actions on each other.

As the combination of the ligand and the intended substance to be adsorbed, there can be mentioned a combination of an enzyme and a substrate, product, inhibitor, coenzyme or effector, a combination of an antigen and an antibody, a combination of a receptor and an agonist, a pair of a nucleic acid and a base, a combination of lectin and a saccharide or glycoprotein, a combination of a metal chelate and a protein, a combination of a hydrophobic group and a protein, a combination of a host and a guest, and a combination of protein A and immunoglobulin G (IgG).

In the separation, purification or analysis by affinity chromatography, the active support, which is the main constituent of the adsorbent for the affinity chromatography, must have the following properties. Namely, a small non-specific adsorption, a high porosity, an easily accomplished bonding of the ligand, a large fixation-capacity, a high chemical stability such that the support is stable and a change of the volume does not occur within broad ranges of the pH value, salt concentration and temperature, a support having a required mechanical strength and stability, good flowability characteristics, and a high resistance to biological contamination.

Cellulose, dextran, polyacrylamide and agarose customarily used as the substrate of the adsorbent for the affinity chromatography do not possess all of these required properties. In particular, since they are soft gels having a poor hardness, their flowability characteristics and separation characteristics are not satisfactory. Moreover, they have a very short life.

The silica beads recently used have a satisfactory hardness, but since they cannot be used under alkaline conditions, selection of the separation conditions or the eluting and washing conditions is considerably restricted.

It is known that protein A adsorbs IgG or an immune complex (Immunochemistry, vol. 7, pages 124 through 127), and it is also known that an immune complex acts as a blocking factor in the immune system. Accordingly, it is presumed that the adsorption of the immune complex by an adsorbent bearing protein A is related to the activation of the immune system, but the action of protein A on an interleukin-2 (IL-2) inhibitor and immunosuppresive substances has not been fully elucidated. As one specific and practical medical application of protein A, a fixation of protein A to an appropriate carrier has been attempted: For example, there have been proposed an adsorbent formed by coating protein A on the surface of active carbon, an adsorbent formed by embedding protein A in a collodion membrane (Engl. J. Med., 305, 1195, 1981), and an adsorbent formed by fixing protein A to a polysaccharide such as agarose or dextran or a plastic material such as polystyrene.

However, these adsorbents have the following problems.

(1) The amount of protein A fixed is small and the adsorption capacity is low.

(2) The fixation of the protein A is not stable, and there is a risk of a leakage of the protein A or the production of a harmful side effect on a human body.

(3) Since the carrier has a poor affinity with a living body, coagulation is often caused by contact with a body fluid such as blood.

(4) If a carrier has a high hydrophobic property, such as a polystyrene carrier, albumin, globulin and the like are non-specifically adsorbed and the capacity of selective adsorption by protein A is reduced.

When protein A is fixed by ionic adsorption, physical adsorption or embedding, leakage of the protein A occurs and it is possible that this will prove harmful to the human body. Accordingly, the development of a method for fixing protein A quantitatively and stably on a carrier is required. On the other hand, if the supporting carrier is recognized as a foreign substance in a living body, blood is coagulated or an antibody is induced around the carrier. Accordingly, the contact with blood is inhibited and the effect is reduced, and clots of coagulated blood migrate in the blood vessel and produce thrombus in a narrow portion thereof. Therefore, it is possible that this could have a serious effect dangerous to a living body.

SUMMARY OF THE INVENTION

It is a primary object of the present invention to provide an adsorbent for affinity chromatography, which has all of the above-mentioned properties required for an adsorbent for affinity chromatography.

Another object of the present invention is to provide an adsorbent capable of selectively adsorbing an IL-2 inhibitor or immunoglobulin without producing a harmful side effect.

In accordance with one aspect of the present invention, there is provided an adsorbent composed of porous beads of uncrosslinked or crosslinked chitosan, wherein protein A or lectin is covalent-bonded through a combination group to the amino group of glucosamine constituting the chitosan in the case of uncrosslinked chitosan or to the amino group of glucosamine constituting the chitosan and an amino group of a crosslinking agent in the case of crosslinked chitosan.

In accordance with another aspect of the present invention, there is provided a method for adsorbing and removing an IL-2 inhibitor by using the above-mentioned adsorbent composed of porous beads of uncrosslinked or crosslinked chitosan to which protein A is bonded through a combination group.

In accordance with still another aspect of the present invention, there is provided a method for adsorbing an intended substance by affinity chromatography using the above-mentioned adsorbent composed of porous beads of uncrosslinked or crosslinked chitosan to which protein A or lectin is bonded through a combination group.

In accordance with still another aspect of the present invention, there is provided a carrier for the chromatography, which is composed of porous beads of uncrosslinked or crosslinked chitosan, wherein an ω-carboxylalkanoyl group is bonded to the amino group of glucosamine constituting the chitosan in the case of uncrosslinked chitosan or to at least a part of the amino group of glucosamine constituting the chitosan and an amino group of a crosslinking agent in the case of crosslinked chitosan, and the remaining unreacted amino group is acylated.

In accordance with still another aspect of the present invention, there is provided a method for adsorbing immunoglobulin by using an adsorbent composed of porous beads of uncrosslinked or crosslinked chitosan.

BRIEF DESCRIPTION OF THE DRAWINGS

FIGS. 8 and 9 are photographs showing the results obtained when the capacity of adsorbing immunoglobulin in human plasma by an adsorbent of the present invention is determined by immunoelectrophoresis; and, FIGS. 10 and 11 are photographs showing the results obtained when the capacity of adsorbing immunoglobulin in human plasma by an adsorbent of the present invention is determined by immunodiffusion.

DESCRIPTION OF THE PREFERRED EMBODIMENTS

Figure 1:
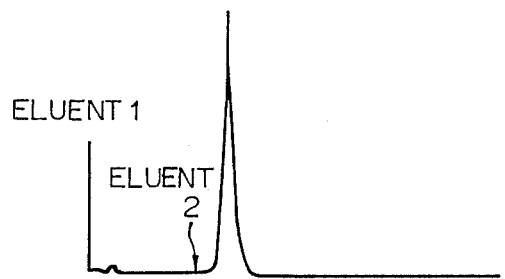
FIG. 1 is a chromatogram showing the results of the analysis of human IgG by using a protein A-supported adsorbent composed of porous beads of chitosan.

The chitosan porous bead used in the present invention is composed of polyglucosamine obtained by deacetylating chitin, which is contained in a sclerite of a crustacean or insect, or a crosslinked product of such polyglucosamine.

The crosslinked product has superior chemical characteristics, such as acid resistance and mechanical strength characteristics, to the uncrosslinked chitosan. As the crosslinking agent, preferably dicarboxylic acids and halides thereof represented by the following formula (I) are used:

wherein X represents a chlorine or bromine atom or a hydroxyl group, Y represents a cyclohexylene, phenylene, methylphenylene or dimethylphenylene group, m is 0 or 1, and n is 0 or an integer of from 1 to 7, dialdehydes represented by the following formula (II):

wherein Y, m and n are as defined above, and diisocyanates represented by the following formula (III):

$$OCN-(CH_2)_n-(Y)_m-(CH_2)_n-NCO \quad (III)$$

wherein Y, m and n are as d above.

The crosslinking is performed by reacting chitosan with the crosslinking agent in an amount of 0.2 to 2.0 moles per mole of the glucosamine group of chitosan in the presence of a polar solvent, for example, an alcohol such as methanol, ethanol or isopropanol, a ketone such as acetone or an amide such as dimethylformamide.

The uncrosslinked chitosan porous bead has an amino group based on glucosamine in an amount of several micromoles/gram to several millimoles/gram, and the crosslinked chitosan porous bead has both an amino group based on glucosamine and an amino group based on the crosslinking agent in a total amount of several micromoles/gram to several millimoles/gram. Preferably, the average particle diameter of the chitosan porous bead is 0.1 to 3 mm, and the shape thereof is spherical. In view of the surface area and strength of the adsorbent, preferably, the chitosan porous bead has fine pores having an average diameter of 0.05 to 3 μm.

The uncrosslinked or crosslinked chitosan porous bead can be used as an adsorbent for the removal of immunoglobulin. Namely, an adsorbent composed of the chitosan porous bead is harmless to a living body and has a capacity of selectively adsorbing immunoglobulin in the body fluid, and this adsorbent exhibits a good adsorption capacity per unit weight and does not cause a coagulation of blood. It is expected hat, when this adsorbent is used for the external circulation of a body fluid, a satisfactory effect will be attained in the remedy of immunity-related diseases.

The amino group of glucosamine constituting the chitosan in the case of uncrosslinked chitosan, or both the amino group of glucosamine constituting the chitosan and the amino group of the crosslinking agent in the case of crosslinked chitosan, can be converted to a combination group having a carboxyl group by reaction with an alkane-dicarboxylic anhydride.

As the alkane-dicarboxylic anhydride used for the reaction, there can be mentioned those having 4 to 16 carbon atoms, such as succinic anhydride, glutaric anhydride, adipic anhydride, pimelic anhydride, suberic anhydride, azelaic anhydride, sebacic anhydride, 1,10-decane-dicarboxylic anhydride, 1,12-dodecanedicarboxylic anhydride, and 1,14-tetradecane-dicarboxylic anhydride.

Preferably, the amount of the carboxyl group introduced from the alkane-dicarboxylic anhydride is 0.01 to 2.0 millimoles/gram of the chitosan porous bead.

The reaction conditions are not particularly critical, but generally, the following conditions are preferably selected for the reaction.

Namely, the weight ratio (a)/(b) of the chitosan porous bead (a) to the alkane-dicarboxylic anhydride (b) is from 1/0.05 to 1/10, more preferably from 1/0.1 to ½, the reaction temperature is 0° to 150° C., more preferably room temperature to 100° C., the reaction time is 1 to 60 hours, more preferably 1 to 30 hours, and the reaction pressure is atmospheric pressure to 10 atmospheres, more preferably atmospheric pressure.

Water is ordinarily used as the reaction solvent, but ethers such as tetrahydrofuran and dioxane, carboxylic acids such as acetic acid and pyridine also can be used. A catalyst need not be used, but the pH value of the reaction liquid can be adjusted by the addition of an acid such as hydrochloric acid or sulfuric acid or a base such as sodium hydroxide or potassium carbonate.

Conditions for the treatment after the reaction are not particularly critical. Namely, the post treatment can be accomplished by a customary means such as filtration or washing.

The so-obtained chitosan porous bead having a carboxyl group is further reacted with a monocarboxylic anhydride or acyl halide to acylate substantially all of the unreacted amino group. If the acylation is not carried out, a non-specific interaction occurs because of the basicity of the unreacted amino group, and it is difficult to attain the intended object.

The conditions for this reaction may be the same as the above-mentioned conditions for the reaction with the alkane-dicarboxylic anhydride. However, where an acyl halide is used as the acylating agent, a solvent other than water is preferably used, and a base is preferably used as the catalyst.

As the monocarboxylic anhydride used in the present invention, there can be mentioned those having 4 to 12 carbon atoms, such as acetic anhydride, propionic anhydride, and butyric anhydride, and as the acyl halide used in the present invention, there can be mentioned those having 2 to 6 carbon atoms, such as acetyl chloride, acetyl bromide, propionyl chloride, and butyryl chloride.

If a combination group having a carboxyl group is introduced in the uncrosslinked or crosslinked chitosan porous bead and the acylation is then carried out as described above, a ligand for affinity chromatography such as protein A or lectin, can be easily covalent-bonded to the chitosan through the combination group having a carboxyl group. Accordingly, this chitosan porous bead is very valuable as a water-insoluble active support for affinity chromatography.

As the ligand covalent-bonded to the carboxyl group, there can be mentioned protein A and lectin. The kind of lectin to be bonded is not particularly critical. For example, there can be mentioned plant lectins such as concanavalin A, Indian licorice lectin, wheat germ lectin, castor bean lectin, soybean lectin, gorse seed lectin, red kidney bean lectin, asparagus pea lectin, bandelia bean lectin, lentil lectin, pea lectin and peanut lectin, and animal lectins such as horseshoe crab lectin, eel lectin and snail lectin. As the protein A as the ligand, there can be used protein A obtained from the cell wall of a *staphylococcus aureus,* or protein A produced from *Eschrishia coli* or yeast by genetic engineering.

Protein A or lectin can be covalent-bonded to the carboxyl group by the treatment with a condensing agent such as dicyclohexylcarbodiimide or 1-ethyl-3-(3-dimethylaminopropyl)carbodiimide singly or in combination with a condensing agent such as N-hydroxysuccinamide in an appropriate solvent. Water is generally used as the solvent. A phosphate or acetate buffer can be used according to need, or an inorganic salt such as sodium chloride can be added.

The conditions for the reaction with protein A or lectin are not particularly critical, but the following conditions are generally preferred.

The weight ratio of the carboxyl group-bonded chitosan porous bead of the present invention to protein A or lectin is from 1/0.03 to 1/0.3, preferably from 1/0.05 to 1/0.2, the reaction temperature is 0° C. to room temperature, preferably 4° C. to room temperature, and the reaction time is 1 to 72 hours, preferably 2 to 12 hours.

The conditions for the post treatment after the reaction are not particularly critical, and the post treatment is appropriately accomplished by customary means such as filtration or washing.

The amount of protein A or lectin bonded is generally about 1 mg/g to about 30 mg/g of the chitosan porous bead.

The adsorbent composed of the chitosan porous bead having protein A or lectin bonded thereto is valuable as an adsorbent for the affinity chromatography. The adsorbent composed of the chitosan porous bead having protein A bonded thereto also is valuable as an adsorbent for adsorbing and removing an IL-2 inhibitor.

The adsorbent of the present invention can be used as a packing for affinity chromatography in the same way as a conventional adsorbent composed of a soft gel, and the adsorbent can be used even under pressure when packed in a pressure-resistant column. Accordingly, the operation time can be greatly shortened and the efficiency of the separation and purification highly improved: This advantage is indispensable for application to high performance liquid chromatography or application to industrial separation and purification equipment.

In the preferred adsorption carrier for the chromatography according to the present invention, since the unreacted amino group of the chitosan porous bead is completely acylated, ionic non-specific adsorption is eliminated on contact with a protein or the like and the selectivity for adsorption of the intended substance by the ligand is greatly enhanced. Furthermore, this adsorbent is advantageous over a conventional adsorbent for affinity chromatography, which has a ligand bonded through cyanogen bromide or glutaraldehyde, in that leakage of the ligand during the operation is minimized and since the length of the bonding group can be optionally adjusted, the adsorption capacity of the ligand to the intended substance is increased and non-specific adsorption is controlled.

Furthermore, in the protein A-supported adsorbent of the present invention to be used for removing an IL-2 inhibitor, a sufficient amount of protein A can be supported without reduction of the activity of protein A. Moreover, since protein A is not leaked during the operation and non-specific adsorption is avoided, the adsorbent is very stable and can be used with a high efficiency.

The present invention will now be described in detail with reference to typical examples of the method for preparing the adsorption carrier for chromatography. However, these examples are only illustrative and by no means limit the scope of the invention.

EXAMPLE 1

A solution of 1.0 g of glutaric anhydride in 5 ml of water was added to 1.0 g of a xylylene diisocyanate-crosslinked chitosan porous bead having an average particle diameter of 0.1 mm and an average pore diameter of 0.07 $\mu$m (Shodex Chitopearl supplied by Showa Denko K.K.), and the pH value was adjusted to 6 by a 4N aqueous solution of sodium hydroxide. The mixture was shaken at room temperature for one day, and the bead was then recovered by filtration and washed with a 0.1N aqueous solution of sodium hydrogencarbonate, 0.1N hydrochloric acid and then with water. Then, 5 ml of a 0.2 M aqueous solution of sodium acetate was added to the bead and 0.5 g of acetic anhydride was further added, and the mixture was shaken at room temperature for 2 hours to effect acetylation of the remaining amino group. The bead was recovered by filtration, washed with a large quantity of water, and dried. According to the cholorimetry using sodium trinitrobenzene-sulfonate, it was confirmed that the bead did not contain amino groups. This bead (containing 0.35 millimole of the carboxyl group per gram of the dry bead) (1.0 g) was washed with anhydrous dioxane and then added to 4 ml of anhydrous dioxane, and 80 mg of N-hydroxysuccinic acid imide and 144 mg of dicyclohexylcarbodiimide were further added and the mixture was shaken at room temperature for 2 hours. The bead was recovered by filtration and promptly washed with 20 ml of anhydrous dioxane, 6 ml of methanol, and then 3 ml of cold water.

The bead was added to 2 ml of a 0.01M aqueous solution of sodium hydrogencarbonate containing 6 mg of protein A. The mixture was shaken at room temperature for 2 hours and allowed to stand at 4° C. overnight. The bead was recovered by filtration and washed with a 1 M aqueous solution of sodium chloride and then with water, and the bead was then added to 2 ml of a 1 M trishydrochloric acid buffer solution (pH 8.0) and the mixture shaken at room temperature for 1 hour. The bead was then recovered by filtration and washed with water.

From the amount recovered of unreacted protein A, it was confirmed that, in the obtained adsorbent, protein A was supported in an amount of 3.0 mg per gram of the dry bead.

EXAMPLE 2

An adsorbent having protein A supported in an amount of 3.5 mg per gram of the dry bead was prepared in the same manner as described in Example 1 except that a hexamethylene diisocyanate-crosslinked chitosan porous bead having an average pore diameter of 0.07 $\mu$m (Shodex Chitopearl) was used instead of the crosslinked chitosan porous bead (Shodex Chitopearl) used in Example 1.

EXAMPLE 3

With respect to each of the protein A-supported crosslinked chitosan bead adsorbents prepared in Examples 1 and 2, the adsorption capacity for an IL-2 inhibitor was tested in the following manner.

To 0.1 g of the bead was added 0.4 ml of an aqueous solution containing 5% by weight of IL-2, and the mixture was incubated at 37° C. for 60 minutes. The product was subjected to centrifugal separation at 2000$\times$g for 2 to 5 minutes, and the supernatant was passed through a bacteria-removing filter having a mesh size of 0.22 $\mu$m. Then, 0.05 ml of the obtained liquid was added to 0.05 ml of an IL-2-dependent cultured cell NKC-7 suspension containing 2$\times 10^6$ cells per ml and containing 10% of bovin fetal serum, and incubation was carried out at 37° C. for 24 hours in an incubator containing 5% of $CO_2$. Four hours before stopping of the reaction, up-taking was carried out by addition of 0.025 ml of $^3$H-thymidine having a concentration of 25 $\mu$c/ml and CPM was measured by a $\beta$-counter. The absorption ratio (%) was calculated according to the following equation:

$$\text{Adsorption ratio (\%)} = \left(1 - \frac{\text{measured value (CPM)}}{\text{control value (CPM)}}\right) \times 100$$

Note: control value was determined in the same manner as mentioned above except that the bead was not used.

The so-determined adsorption ratios (%) of the adsorbents obtained in Examples 1 and 2 were $-42.9\%$ and $-33.8\%$, respectively. For reference, the adsorption ratios (%) of the chitosan beads used in Examples 1 and 2 were $+13.5\%$ and $+12.2\%$, respectively.

EXAMPLE 4

A protein A-supported crosslinked chitosan bead adsorbent was prepared in the same manner as in Example 1 except that the amount of protein A was changed to 10 mg. From the amount recovered of unreacted protein A, it was confirmed that 6.0 mg of protein A was supported per gram of the dry bead.

The so-obtained adsorbent was packed in a stainless steel column having a diameter of 8 mm and a length of 50 mm, and human IgG was analyzed by using a high performance liquid chromatograph to obtain a chromatogram shown in FIG. 1. The analysis conditions were as follows.

Eluent (1): 0.01 M sodium acetate/hydrochloric acid buffer (pH 7.0)
Eluent (2): 0.01 M sodium acetate/hydrochloric acid buffer (pH 3.0)
Elution rate: 0.5 ml/min
Detector: ultraviolet spectrophotometer, 280 nm

COMPARATIVE EXAMPLE 1

Figure 2:
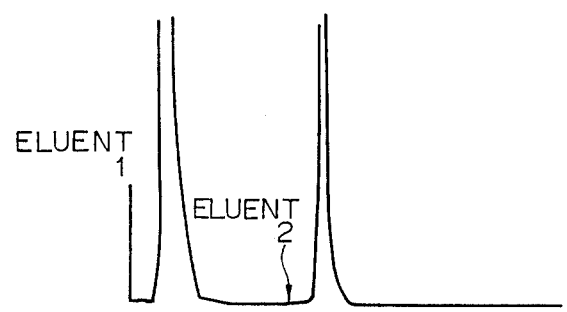
FIG. 2 is a chromatogram showing the results of the analysis of human serum by using an adsorbent composed of porous beads of chitosan containing a non-acylated amino group.
Figure 3:
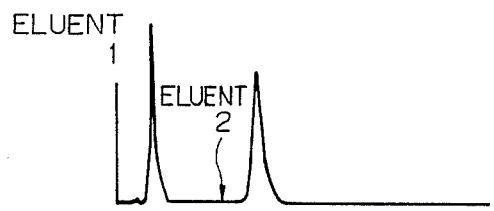
FIG. 3 is a chromatogram illustrating the results obtained when a fraction adsorbed by an eluent (1) and eluted by an eluent (2) is analyzed again by the adsorption column of the adsorbent of the present invention.

By using the chitosan bead adsorbent having an un-acylated amino group, which was obtained midway in the process for the production of the adsorbent of Example 1, human serum was analyzed instead of human IgG according to the method described in Example 4 to obtain a chromatogram shown in FIG. 2. When the fraction eluted by the eluent (2) was analyzed again by the column described in Example 4, a peak of the fraction eluted by the eluent (1) was observed (see FIG. 3).

It is deemed that this peak was attributed to the protein ionically bonded non-specifically to the free amino group.

EXAMPLE 5

An adsorbent was prepared in the same manner as described in Example 1 except that concanavalin A was supported instead of protein A according to the following procedures.

Namely, the bead just before the treatment with the protein A solution in Example 1 was added to a solution of 30 mg of concanavalin A and 40 mg of methyl-$\alpha$-mannopyranoside in 2 ml of water containing 0.1 mM calcium chloride, 0.1 mM manganese chloride and 0.01 mM sodium hydrogencarbonate. The mixture was shaken at room temperature for 2 hours and allowed to stand at 4° C. overnight. The bead was recovered by filtration, washed with a 1 M aqueous solution of sodium chloride and then with water, and added to 2 ml of a 1 M tris-hydrochloric acid buffer (pH 8.0), and the mixture was shaken at room temperature for 1 hour. The bead was recovered by filtration and washed with water. From the amount of recovered unreacted concanavalin A, it was confirmed that concanavalin A was supported in an amount of 15 mg per gram of the dry bead.

The so-obtained adsorbent was packed in a stainless steel column having a diameter of 8 mm and a length of 50 mm, and p-nitrophenyl-$\alpha$-D-galactopyranoside (compound 1) and p-nitrophenyl-$\alpha$-D-mannopyranoside (compound 2) were analyzed by a high performance liquid chromatograph. The results are shown in Table 1.

TABLE 1

Figures 4, 5:
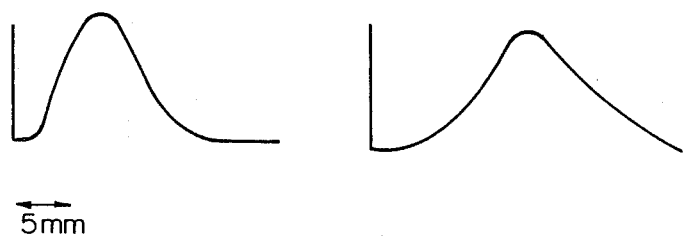
FIGS. 4 and 5 show the results obtained by examining an elution of p-nitrophenyl-α-D-galactopyranoside and p-nitrophenyl-α-D-mannopyraside by using a concanavalin A-supported adsorbent of the present invention.

| Compound | Retention Capacity (ml) |
| --- | --- |
| 1 | 9 ml (FIG. 4) |
| 2 | 15 ml (FIG. 5) |

Note, the analysis was carried out under the following conditions.

Eluent: 0.02 M tris-hydrochloric acid buffer containing 0.5 M sodium chloride, 0.5 mM calcium chloride and 0.5 mM manganese chloride (pH 7.4)
Elution rate: 1.0 ml/min
Detector: ultraviolet spectrophotometer, 260 nm

COMPARATIVE EXAMPLE 2

By using the unacylated amino group-containing chitosan bead adsorbent, obtained midway in the process for the production of the adsorption carrier of Example 5, egg albumin was analyzed according to the method described in Example 5 under the following conditions.

Figure 6:
FIGS. 6 and 7 show patterns obtained by examining the adsorption and elution of egg albumin by using an adsorbent containing a non-acrylated amino group, obtained in Comparative Example 2, and an adsorbent according to the present invention.

Eluent (A): 0.01 M sodium phosphate buffer (pH 7.0)
Eluent (B): eluent (A) plus 0.05 M $\alpha$-methylglucoside
Elution rate: 1.0 ml/min
Detector: ultraviolet spectrophotometer, 280 nm When the eluent (A) was used, the majority of egg albumin was adsorbed, and when the eluent (A) was switched to the eluent (B), a part of the adsorbed egg albumin was eluted but a considerable portion was remained adsorbed (see FIG. 6).

Figure 7:
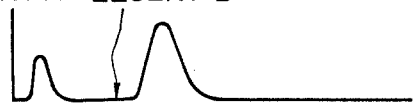

Then, the egg albumin was analyzed in the same manner as described above by using the adsorbent obtained in Example 5. The majority of the egg albumin adsorbed by the eluent (A) was eluted by the eluent (B) (see FIG. 7). When the same amount of egg albumin was analyzed, there was a definite difference of the eluted amount between FIGS. 6 and 7, and this was considered due to the influence of the unacylated amino group.

EXAMPLE 6

An adsorption carrier having wheat germ lectin supported in an amount of 3.2 mg per gram of the dry bead was obtained in the same manner as described in Example 5 except that a solution of 5.0 mg of wheat germ lectin and 10 mg of N-acetyl-$\alpha$-glucosamine in 3 ml of water containing 0.05 M potassium phosphate, 0.15 M sodium chloride, and 0.01 M sodium hydrogencarbonate was used instead of the solution containing 30 mg of concanavalin A used in Example 5.

EXAMPLE 7

In the process for the production of the adsorbent of Example 1, 1.0 g of the glutaric anhydride-treated and acetic anhydride-treated bead (the carboxyl group content was 0.35 millimole per gram of the dry bead) was washed with anhydrous dioxane and was then added to 4 ml of anhydrous dioxane, and 80 mg of N-hydroxysuccinic acid imide and 144 mg of dicyclohexylcarbodiimide were further added. The resultant mixture was shaken at room temperature for 2 hours. Then, the bead was recovered by filtration and promptly washed with 20 ml of anhydrous dioxane, 6 ml of methanol, and then 3 ml of cold water. Then, the bead was added to a solution of 30 mg of concanavalin A and 40 mg of methyl-$\alpha$-mannopyranoside in 2 ml of water containing 0. mM calcium chloride, 0.1 mM manganese chloride and 0.01 M sodium hydrogencarbonate. The resultant mixture was shaken at room temperature for 2 hours and allowed to stand at 4° C. overnight. The bead was recovered by filtration, washed with a 1 M aqueous solution of sodium chloride and then with water and added to 2 ml of a 1 M tris-hydrochloric acid buffer (pH 8.0), and the mixture was shaken at room temperature for 1 hour. Then, the bead was recovered by filtration and washed with water. From the amount recovered of unreacted concanavalin A, it was confirmed that concanavalin A was supported on the adsorbent in an amount of 15 mg per gram of the dry bead.

EXAMPLE 8

A solution of 0.1 g of succinic anhydride in 5 ml of dioxane was added to 1.0 g of a hexamethylene diisocyanate-crosslinked chitosan porous bead having an average particle diameter of 0.3 mm and an average pore diameter of 0.07 $\mu$m (Shodex Chitopearl supplied by Showa Denko K.K.), and 0.1 g of pyridine was further added. The resultant mixture was shaken at room temperature for 6 hours. The bead was recovered by filtration and washed with dioxane, and a solution of 0.5 g of acetyl chloride in 5 ml of dioxane was added to the bead. Then, 0.5 g of triethylamine was further added to the mixture, and the resulting mixture was shaken at room temperature for 30 minutes. The bead was recovered by filtration, washed with water and then with a large quantity of dioxane and dried. It was confirmed by cholorimetry using sodium trinitrobenzene-sulfonate that the bead did not contain amino groups. The amount of the carboxylic acid determined by the neutralization titration was 0.80 millimole per gram of the dry bead.

By using this bead, an adsorbent having protein A supported in an amount of 6.0 mg per gram of the dry bead was prepared in the same manner as described in Example 7 except that a solution of 10 mg of protein A in 2 ml of water containing 0.01 M sodium hydrogencarbonate was used instead of the solution containing 30 mg of concanavalin A, used in Example 7.

EXAMPLE 9

To 10 ml of human plasma was added 1 ml of a wet adsorbent of (A) a hexamethylene diisocyanate-crosslinked chitosan porous bead having an average particle diameter of 0.1 mm and an average pore diameter of 0.07 μm (Shodex Chitopearl supplied by Showa Denko K.K.) or (B) a xylylene diisocyanate-crosslinked chitosan porous bead having the same average particle diameter and pore diameter (Shodex Chitopearl supplied by Showa Denko K.K.), and incubation was carried out at 4° C. or 37° C. for 1 hour and the bead was recovered by centrifugation. The bead was washed three times with 1 ml of a saline and was combined with the supernatant. The changes of the total protein (T.P.), albumin (Alb), total cholesterol (T. Cho), IgM, IgA and IgM contents were examined by the high performance liquid chromatography. The results are shown in Table 2.

TABLE 2

|  |  | T.P. (g/dl) | Alb (g/dl) | T.Cho (mg/dl) | IgG (mg/dl) | IgA (mg/dl) | IgM (mg/dl) |
|---|---|---|---|---|---|---|---|
| Plasma before treatment |  | 6.6 | 4.4 | 121 | 1760 | 246 | 175 |
| 4° C. | (A) | 5.9 | 4.2 | 105 | 1220 | 172 | 117 |
|  | (B) | 5.9 | 4.1 | 104 | 1420 | 194 | 139 |
| 37° C. | (A) | 5.7 | 4.0 | 100 | 1350 | 188 | 134 |
|  | (B) | 5.8 | 4.0 | 100 | 1180 | 159 | 114 |

EXAMPLE 10

The bead (B) obtained in Example 9 was mixed with human plasma at a mixing ratio shown in Table 3 and incubation was carried out at 37° C. for 30 minutes. The supernatant recovered by centrifugation was evaluated with respect to the specific adsorbing characteristic by the immunoelectrophoresis. The capacity of adsorbing immunoglobulin in human plasma as determined by the immunoelectrophoresis is shown in the photographs in FIGS. 8 and 9. It was confirmed that the bead specifically adsorbed the globulin region, compared with the control.

TABLE 3

| Sample | Adsorbent | Human Plasma |
|---|---|---|
| (1) Wet adsorbent of (B) | 0.1 g | 0.2 ml |
| (2) Dry adsorbent of (B) | 0.1 g | 1.0 ml |
| (3) Re-wetted adsorbent of (2) | 0.1 g[1] | 1.0 ml |

Note
(1) 0.1 g of the sample (2) was re-wetted with a saline.

EXAMPLE 11

The IgG adsorption ratios of the samples described in Example 10 were determined by testing according to the immunodiffusion method. The capacity of adsorbing immunoglobulin in human plasma as determined by the immunodiffusion is shown in the photographs in FIGS. 10 and 11, and in Table 4.

TABLE 4

| Sample | Diffusion area (mm²) | Adsorption ratio (%)[1] | Photograph |
|---|---|---|---|
| Control | 135 | — | FIG. 10 |
| (1) | 90 | 33 | FIG. 10 |
| (2) | 57 | 58 | FIG. 10 |
| Control | 90 | — | FIG. 11 |
| (2) | 26 | 71 | FIG. 11 |
| (3) | 23 | 74 | FIG. 11 |

Note

[1] adsorption ratio = $\left(1 - \dfrac{As}{Ac}\right) \times 100$

Ac: area in control
As: area in sample

We claim:

1. An adsorbent composed of porous beads of crosslinked chitosan constituted of glucosamine, having protein A or a lectin covalently bonded to said porous beads of crosslinked chitosan, wherein said crosslinked chitosan is obtained by crosslinking uncrosslinked chitosan with a crosslinking agent selected from the group consisting of dicarboxylic acids and halides thereof represented by formula (I):

wherein X represents a chlorine or bromine atom or a hydroxyl group; Y represents a cyclohexylene, phenylene, methylphenylene or dimethylphenylene group; m is 0 or 1, and n is 0 or an integer of from 1 to 7;

and diisocyanates represented by formula (III);

wherein Y, m and n are as defined above;

said protein A or lectin being covalently bonded via a bonding group to at least a part of the amino groups of the glucosamine constituting said chitosan and at least a part of the amino groups of said crosslinking agent of the formula (III) when present, said bonding group comprising a combination group having a carboxyl group introduced by reaction of said amino groups with an alkane-dicarboxylic anhydride having from 4 to 16 carbon atoms; provided that substantially all of the amino groups other than the amino groups to which said protein A or lectin is covalently bonded via the combination group are acylated with an acyl group having from 2 to 6 carbon atoms.

2. An adsorbent as set forth in claim 1, wherein the chitosan porous beads have an average particle diameter of 0.1 to 3 mm.

3. An adsorbent as set forth in claim 1, wherein the chitosan porous beads have pores having an average pore diameter of 0.05 to 3 μm.

4. An adsorbent as set forth in claim 1, wherein the amount of the carboxyl group is 0.01 to 2.0 millimoles per gram of the chitosan porous beads.

5. An adsorbent as set forth in claim 1, wherein the amount of the covalent-bonded protein A or lectin is 1 to 30 mg per gram of the chitosan porous bead.

6. A carrier for use in chromatography, composed of porous beads of crosslinked chitosan constituted of glucosamine, wherein said crosslinked chitosan is obtained by crosslinking uncrosslinked chitosan with a crosslinking agent selected from the group consisting of dicarboxylic acids and halides thereof represented by formula (I):

(I)

wherein X represents a chlorine or bromine atom or a hydroxyl group; Y represents a cyclohexylene, phenylene, methylphenylene or dimethylphenylene group; m is 0 or 1, and n is 0 or an integer of from 1 to 7;

and diisocyanates represented by formula (III):

(III)

wherein Y, m and n are as defined above; wherein
an ω-carboxylalkanoyl group is bonded to at least a part of the amino groups of the glucosamine constituting the chitosan and at least a part of the amino groups of said crosslinking agent of the formula (III) when present bonded to the chitosan, provided that the remaining unreacted amino groups are acylated.

7. A carrier as set forth in claim 6, wherein the chitosan porous beads have an average particle diameter of 0.1 to 3 mm.

8. A carrier as set forth in claim 6, wherein the chitosan porous beads have pores having an average pore diameter of 0.05 to 3μm.

9. A carrier as set forth in claim 6, wherein the amount of the ω-carboxyalkanoyl group is 0.01 to 2.0 millimoles per gram of the chitosan porous beads.

10. A method for adsorbing and removing an interleukin-2 inhibitor from a fluid containing said inhibitor, comprising contacting said fluid with an adsorbent composed of porous beads of crosslinked chitosan constituted of glucosamine and having protein A bonded to said porous beads of crosslinked chitosan, wherein said crosslinked chitosan is obtained by crosslinking uncrosslinked chitosan with a crosslinking agent selected from the group consisting of dicarboxylic acids and halides thereof represented by formula (I):

(I)

wherein X represents a chlorine or bromine atom or a hydroxyl group; Y represents a cyclohexylene, phenylene, methylphenylene or dimethylphenylene group; m is 0 or 1; and n is 0 or an integer of from 1 to 7;

and diisocyanates represented by formula (III):

(III)

wherein Y, m and n are as defined above;
said protein A being covalently bonded via a bonding group to at least a part of the amino groups of the glucosamine constituting said chitosan and at least a part of the amino groups of said crosslinking agent of the formula (III) when present bonded to said chitosan, said bonding group comprising a combination group having a carboxyl group introduced by reaction of said amino groups with an alkane-dicarboxylic anhydride having from 4 to 16 carbon atoms; provided that
substantially all of the amino groups other than the amino groups to which said protein A is bonded via the combination group having the carboxyl group are acylated with an acyl group having from 2 to 6 carbon atoms,
wherein said contacting is for a time sufficient to allow for the adsorption and removal of said interleukin-2 inhibitor from said fluid.

11. A method according to claim 10, wherein the chitosan porous beads have an average particle diameter of 0.1 to 3 mm.

12. A method according to claim 10, wherein the chitosan porous beads have pores having an average pore diameter of 0.05 to 3 μm.

13. A method according to claim 10, wherein the amount of the carboxyl group is 0.01 to 2.0 millimoles per gram of the chitosan porous beads.

14. A method according to claim 10, wherein the amount of the covalent-bonded protein A is 1 to 30 mg per gram of the chitosan porous bead.

15. A method for absorbing an intended substance by affinity chromatography, comprising contacting a fluid containing said substance with an adsorbent comprising porous beads of crosslinked chitosan constituted of glucosamine and having protein A or a lectin covalently bonded to said porous beads of crosslinked chitosan, wherein said crosslinked chitosan is obtained by crosslinking uncrosslinked chitosan with a crosslinking agent selected from the group consisting of dicarboxylic acids and halides thereof represented by formula (I):

(I)

wherein X represents a chlorine or bromine atom or a hydroxyl group; Y represents a cyclohexylene, phenylene, methylphenylene or dimethylphenylene group; m is 0 or 1, and n is 0 or an integer of from 1 to 7, and diisocyanates represented by formula (III):

(III)

wherein Y, m and n are as defined above;
said protein A or lectin being covalently bonded via a bonding group to at least a part of the amino groups of the glucosamine constituting said chitosan and at least a part of the amino groups of the crosslinking agent of formula (III) when present bonded to said chitosan, said bonding group comprising a combination group having a carboxyl group introduced by reaction of said amino groups with an alkane-dicarboxylic anhydride having from 4 to 16 carbon atoms; provided that
substantially all of the amino groups other than the amino groups to which protein A or lectin is bonded via the bonding group are acylated with an acyl group having from 2 to 6 carbon atoms, wherein said contacting is for a time sufficient to allow for the adsorption of said substance to said adsorbent.

16. A method according to claim 15, wherein the chitosan porous beads have an average particle diameter of 0.1 to 3 mm.

17. A method according to claim 15, wherein the chitosan porous beads have pores having an average pore diameter of 0.05 to 3 μm.

18. A method according to claim 15, wherein the amount of the carboxyl group is 0.01 to 2.0 millimoles per gram of the chitosan porous beads.

19. A method according to claim 15, wherein the amount of the covalent-bonded protein A or lectin is 1 to 30 mg per gram of the chitosan porous bead.

20. A method for adsorbing and removing an immunoglobulin from a fluid containing same, comprising contacting said fluid with adsorbent porous beads of crosslinked chitosan constituted of glucosamine, wherein said crosslinked chitosan is obtained by crosslinking uncrosslinked chitosan with a crosslinking agent selected from the group consisting of dicarboxylic acids and halides thereof represented by formula (I):

wherein X represents a chlorine or bromine atom or a hydroxyl group; Y represents a cyclohexylene, phenylene, methylphenylene or dimethylphenylene group; m is 0 or 1; and n is 0 or an integer of from 1 to 7;

and diisocyanates represented by formula (III):

wherein Y, m and n are as defined above.

21. A method according to claim 20, wherein the chitosan porous beads have an average particle diameter of 0.1 to 3 mm.

22. A method according to claim 20, wherein the chitosan porous beads have pores having an average pore diameter of 0.05 to 3 μm.

* * * * *